(12) United States Patent
Suzuki et al.

(10) Patent No.: US 8,460,527 B2
(45) Date of Patent: Jun. 11, 2013

(54) GAS SENSOR

(75) Inventors: Yoshio Suzuki, Nagoya (JP); Kouji Tagawa, Nagoya (JP); Kunihiko Nakagaki, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 474 days.

(21) Appl. No.: 12/036,383

(22) Filed: Feb. 25, 2008

(65) Prior Publication Data

US 2008/0302661 A1    Dec. 11, 2008

(30) Foreign Application Priority Data

Feb. 27, 2007   (JP) ................................. 2007-047408

(51) Int. Cl.
*G01N 27/407* (2006.01)

(52) U.S. Cl.
USPC ........... 204/429; 204/421; 204/424; 204/425; 204/410; 205/783.5

(58) Field of Classification Search
USPC ....... 204/400–435; 205/775–794.5; 73/23.31, 73/23.32
See application file for complete search history.

(56) References Cited

U.S. PATENT DOCUMENTS

| | | | |
|---|---|---|---|
| 4,450,065 A | | 5/1984 | Yamada et al. |
| 4,722,778 A | * | 2/1988 | Hayakawa et al. ........... 204/410 |
| 4,732,663 A | | 3/1988 | Kato et al. |
| 4,919,689 A | | 4/1990 | Pyzik |
| 5,021,372 A | | 6/1991 | Pyzik |
| 5,031,445 A | * | 7/1991 | Kato et al. .................... 73/23.31 |
| 5,118,645 A | | 6/1992 | Pyzik et al. |
| 5,144,249 A | * | 9/1992 | Kurishita et al. ............. 324/439 |
| 6,645,360 B1 | | 11/2003 | Eisele et al. |
| 6,939,607 B2 | | 9/2005 | Kato |
| 7,160,422 B2 | | 1/2007 | Imamura et al. |
| 2002/0060151 A1 | * | 5/2002 | Kato et al. .................... 204/425 |
| 2004/0158971 A1 | * | 8/2004 | Kawashima ................. 29/592.1 |
| 2005/0211554 A1 | * | 9/2005 | Kurachi et al. .............. 204/426 |

FOREIGN PATENT DOCUMENTS

| | | |
|---|---|---|
| DE | 198 15 174 A1 | 10/1999 |
| JP | 58-153155 A1 | 9/1983 |
| JP | 59-156922 | 9/1984 |
| JP | 61-097562 A1 | 5/1986 |
| JP | 01-281858 A1 | 11/1989 |
| JP | 05-169537 A1 | 7/1993 |
| JP | 2786507 B2 | 5/1998 |
| JP | 2000-005992 A1 | 1/2000 |
| JP | 2004-003963 A1 | 1/2004 |
| JP | 2006-201191 A1 | 8/2006 |
| WO | 93/15864 A1 | 8/1993 |

OTHER PUBLICATIONS

U.S. Appl. No. 12/036,393, filed Feb. 25, 2008, Suzuki et al.

* cited by examiner

*Primary Examiner* — Keith Hendricks
*Assistant Examiner* — Susan D Leong
(74) *Attorney, Agent, or Firm* — Burr & Brown

(57) ABSTRACT

A gas sensor contains a sensor element for detecting the concentration of a particular gas component in a measurement gas and a housing for supporting the sensor element inside, and the sensor element has a rectangular solid structure of a solid electrolyte body containing a ceramic material. In the gas sensor, four edges of the solid electrolyte body are beveled over the entire length thereof to form eleventh to fourteenth chamfered portions corresponding to the four edges.

2 Claims, 7 Drawing Sheets

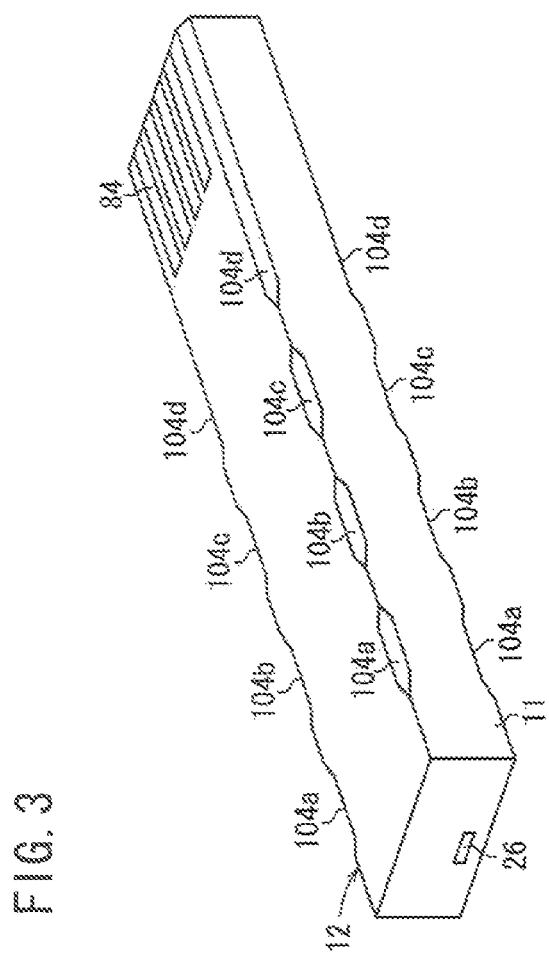

GAS SENSOR

CROSS-REFERENCE TO RELATED APPLICATIONS

This application is based upon and claims the benefit of priority from Patent Application No. 2007-047408 filed on Feb. 27, 2007 in the Japanese Patent Office, of which the contents are incorporated herein by reference.

BACKGROUND OF THE INVENTION

1. Field of the Invention

The present invention relates to a gas sensor comprising a sensor element for detecting the concentration of a specific gas component in a measurement gas and a housing for supporting the sensor element therein, the sensor element having a rectangular solid structure of a solid electrolyte body containing a ceramic material.

2. Description of the Related Art

Among gas sensors, certain oxygen sensors have been known as an oxygen concentration detector. The oxygen sensors are used for detecting the oxygen concentration of an exhaust gas from an internal combustion engine, thereby optimally controlling the combustion state of the engine based on the detected signals, to achieve exhaust gas cleaning, fuel cost reduction, etc.

In one of such oxygen sensors, an oxygen ion-conductive solid electrolyte, such as zirconium oxide doped with calcium oxide, yttrium oxide, or the like, is used for a partition wall. Electrodes are formed on the surfaces of the partition wall to provide a sensor element. One of the electrodes is exposed to a reference atmosphere, the other is exposed to a measurement gas such as an exhaust gas, and an electromotive force generated based on the theory of oxygen concentration cell is obtained as a detection signal.

Among oxygen sensor elements, long plate elements, which have, at one end, an oxygen-detecting section to be exposed to a measurement gas such as an exhaust gas, have recently attracted much attention instead of bottomed cylinder elements. Such long plate elements can be produced and miniaturized easily. Examples of the plate elements are described in Japanese Laid-Open Patent Publication Nos. 58-153155 and 61-097562, etc.

In another oxygen sensor, an oxide such as titanium oxide is disposed on a long plate substrate to provide a sensor element, the electrical resistance of the oxide changing depending on oxygen concentration. The sensor element is exposed to a measurement gas such as an exhaust gas to detect the electrical resistance change depending on the oxygen partial pressure.

In the oxygen sensors, an oxygen-detecting section of an oxygen sensor element is exposed to a measurement gas such as an exhaust gas with high temperature, and the oxygen-detecting section is maintained in some cases at high temperature by a heater built in the oxygen sensor element to achieve sufficient oxygen-detecting function. Thus, the sensor element is subjected to thermal stress. When the sensor element is plate-shaped, the stress is concentrated at the edges, so that the element is often cracked to deteriorate its oxygen concentration-detecting function.

For example, in an oxygen sensor element disclosed in Japanese Patent No. 2786507, edge portions at the end of a plate substrate are chamfered, whereby the stress concentration is relaxed to improve the thermal shock resistance.

The conventional oxygen sensor element disclosed in Japanese Patent No. 2786507 is designed in view of relaxing the concentration of thermal stress.

However, there is a problem that, in an internal combustion engine or the like, the oxygen sensor element is brought into contact with a housing for supporting the oxygen sensor element, particularly with a supporting member for supporting a longitudinal center portion of the oxygen sensor element and a connector for supporting a rear portion of the oxygen sensor element, and the oxygen sensor element is broken by the contact. The problem has to be considered to put the oxygen sensor element into practical use in the internal combustion engine.

SUMMARY OF THE INVENTION

In view of the above problem, an object of the present invention is to further improve the above gas sensor of Japanese Patent No. 2786507 designed for improving thermal shock resistance, thereby providing a more reliable gas sensor that can show a higher thermal shock resistance and can be prevented from breakage by contact with a supporting member of a housing, etc.

The gas sensor of the present invention comprises a sensor element for detecting the concentration of a particular gas component in a measurement gas and a housing for supporting the sensor element therein, the sensor element having a rectangular solid structure of a solid electrolyte body containing a ceramic material. The sensor element comprises a gas inlet for introducing the measurement gas formed at the distal end, an electrode for detecting the gas component formed inside, and a lead wire extending rearward from the electrode. The housing comprises a supporting member for supporting the sensor element, and a connector for supporting the rear portion of the sensor element and for being electrically connected to the lead wire. In the solid electrolyte body of the he sensor element, at least an edge portion in a portion supported by the supporting member and an edge portion in a portion supported by the connector are beveled to form chamfered portions. The chamfered portions have a width of 30 to 240 µm.

Even when the sensor element is exposed to the measurement gas such as an exhaust gas with high temperature or when the sensor element is maintained at high temperature by a heater installed therein, the thermal stress concentration in the solid electrolyte body can be relaxed to improve the thermal shock resistance because the solid electrolyte body of the sensor electrode has the beveled edge portion in the portion supported by the supporting member and the beveled edge portion in the portion supported by the connector.

In the present invention, by controlling the widths of the chamfered portions within the range of 30 to 240 µm, the sensor element can be prevented from the breakage by contact with the housing supporting the sensor element in practical use in an internal combustion engine or the like, to improve the reliability of the gas sensor.

In the present invention, it is preferred that there is a space between the supporting member and the portion to be supported by the supporting member in the solid electrolyte body, and the space has a cross-sectional area of 1.5 to 3.0 mm$^2$. In this case, the sensor element can be certainly prevented from being broken by the contact between the solid electrolyte body and the supporting member for supporting a longitudinal center portion, etc. of the sensor element.

In the present invention, it is preferred there is a space between the connector and the portion to be supported by the connector in the solid electrolyte body, and the space has a cross-sectional area of 1.5 to 3.0 mm². In this case, the sensor element can be certainly prevented from being broken by the contact between the solid electrolyte body and the connector for supporting the rear end of the sensor element.

Further, in the present invention, four edges of the solid electrolyte body may be beveled over the entire length of the body.

As described above, according to the present invention, the oxygen sensor of Japanese Patent No. 2786507 designed for improving thermal shock resistance can be further improved, and there is provided the more reliable gas sensor capable of showing a higher thermal shock resistance and being prevented from the breakage by contact with the supporting member, etc. of the housing.

The above and other objects, features and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 3 is a perspective view showing the shape of a solid electrolyte body in a sensor element of the gas sensor.

DETAILED DESCRIPTION OF THE INVENTION

An illustrative embodiment of the gas sensor of the present invention will be described below with reference to FIGS. 1 to 7.

Figure 1:
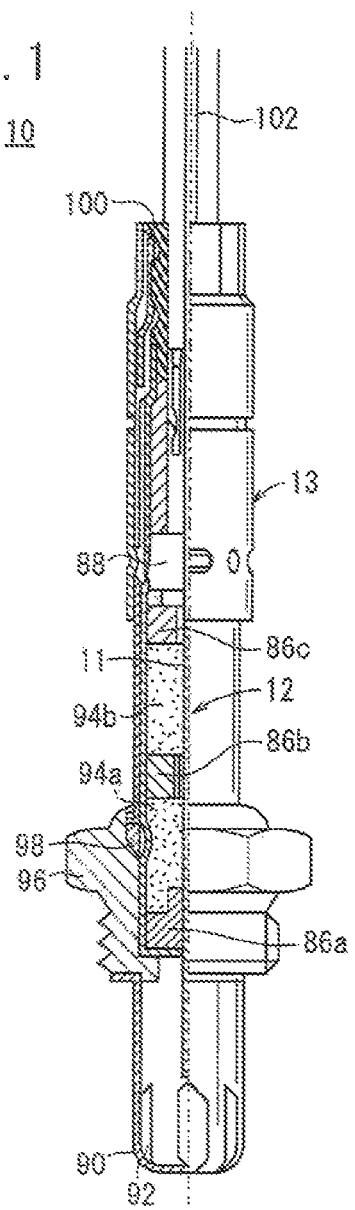
FIG. 1 is a partially broken side view showing a gas sensor according to an embodiment of the present invention.

As shown in FIG. 1, a gas sensor 10 according to this embodiment has a sensor element 12 for detecting the concentration of a particular gas component in a measurement gas and a cylindrical metal housing 13 for supporting the sensor element 12 inside. The sensor element 12 has a rectangular solid structure containing an oxygen ion-conductive, solid electrolyte body 11 of a porcelain zirconia ($ZrO_2$), etc.

Figure 2:
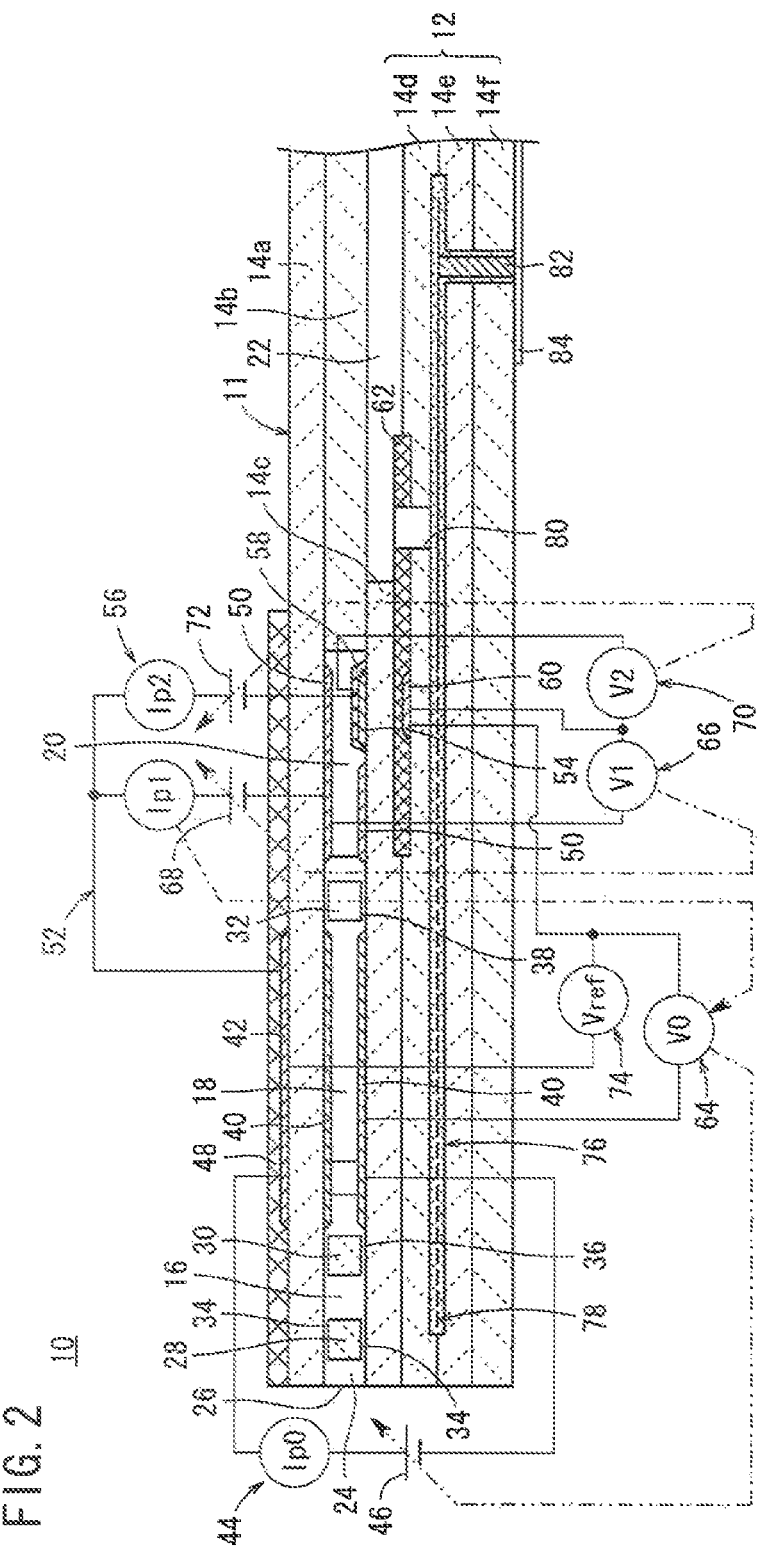
FIG. 2 is a cross-sectional view showing the inner structure of the gas sensor.

As shown in FIG. 2, the sensor element 12 has an integral plate-shaped structure containing a stack of a plurality of dense, airtight, oxygen ion-conductive, solid electrolyte layers (e.g., first to sixth solid electrolyte layers 14a to 14f). Each of the first to sixth solid electrolyte layers 14a to 14f contains a known oxygen ion-conductive solid electrolyte material such as porcelain zirconia ($ZrO_2$). The integral sensor element 12 can be easily formed by a known process of burning a stack of unburned solid electrolyte layers to integrate the layers.

At least four internal spaces (a first internal space 16, a second internal space 18, a third internal space 20, and a fourth internal space 22) are formed in the sensor element 12.

The first to third internal spaces 16, 18, 20 are formed between the first solid electrolyte layer 14a positioned uppermost in FIG. 2 and the third solid electrolyte layer 14c positioned at the third from the top such that the first and third solid electrolyte layers 14a, 14c are stacked and integrated with a spacer of the second solid electrolyte layer 14b in-between.

The first to third internal spaces 16, 18, 20 have heights corresponding to the thickness of the second solid electrolyte layer 14b, and extend in the longitudinal direction of the sensor element 12 between the first and third solid electrolyte layers 14a, 14c as spaces without the second solid electrolyte layer 14b.

Thus, the first to third internal spaces 16, 18, 20, respectively, have rectangular shapes when viewed from the above, are separated from each other, and extend in the longitudinal direction of the sensor element 12 into certain widths, in series.

Among the first to third internal spaces 16, 18, 20, the first internal space 16 is closest to a gas inlet 26 to be hereinafter described, and acts as a buffer space for buffering rapid oxygen concentration change by external pulsation of an exhaust gas. The second internal space 18 acts as a control space for controlling the oxygen partial pressure of the measurement gas, and the third internal space 20 acts as a measurement space for fine-controlling the oxygen partial pressure of the measurement gas and measuring an oxide such as a nitrogen oxide (NOx) in the gas.

The fourth internal space 22 is separated from the first to third internal spaces 16, 18, 20, and extends in the longitudinal direction of the sensor element 12 between the second and fourth solid electrolyte layers 14b, 14d as a space without the third solid electrolyte layer 14c. The fourth internal space 22 acts as a reference gas inlet path for introducing a reference gas into the sensor element 12, and the path is opened at the proximal end of the sensor element 12 to atmospheric air like conventional ones.

Thus, in the following description, the first internal space 16 is referred to as the buffer space 16, the second internal space 18 is referred to as the control space 18, the third internal space 20 is referred to as the measurement space 20, and the fourth internal space 22 is referred to as the reference gas inlet path 22.

A clogging-preventive space 24 opening outward is formed between the first and third solid electrolyte layers 14a, 14c at the outer side of the buffer space 16, i.e. the distal end side of the sensor element 12. The opening of the clogging-preventive space 24 acts as the gas inlet 26 for introducing the external measurement gas into the sensor element 12.

The clogging-preventive space 24 is separated from the buffer space 16 by a first partition wall 28 of the second solid electrolyte layer 14b, the buffer space 16 is separated from the control space 18 by a second partition wall 30 of the second solid electrolyte layer 14b, and the control space 18 is separated from the measurement space 20 by a the third partition wall 32 of the second solid electrolyte layer 14b.

First slits 34 are formed on the upper and lower surfaces of the first partition wall 28 (between the first partition wall 28 and the first solid electrolyte layer 14a, and between the first partition wall 28 and the third solid electrolyte layer 14c), respectively. The first slits 34 act as a first diffusion rate-determining means for the measurement gas. The external measurement gas is introduced from the gas inlet 26 through the clogging-preventive space 24 to the buffer space 16 under a predetermined diffusion resistance of the first slits 34.

Second slits 36 are formed on the upper and lower surfaces of the second partition wall 30 for separating the buffer space 16 and the control space 18 (between the second partition wall 30 and the first solid electrolyte layer 14a, and between the second partition wall 30 and the third solid electrolyte layer 14c), respectively. The second slits 36 act as a second diffusion rate-determining means for the measurement gas. The measurement gas in the buffer space 16 is introduced to the control space 18 under a predetermined diffusion resistance of the second slits 36.

Third slits 38 are formed on the upper and lower surfaces of the third partition wall 32 for separating the control space 18 and the measurement space 20 (between the third partition wall 32 and the first solid electrolyte layer 14a, and between the third partition wall 32 and the third solid electrolyte layer 14c), respectively. The third slits 38 act as a third diffusion rate-determining means for the measurement gas. The measurement gas having a controlled oxygen concentration (partial pressure) in the control space 18 is introduced to the measurement space 20 under a predetermined diffusion resistance of the third slits 38.

In the gas sensor 10 of this embodiment, an inner pumping electrode 40 containing a porous cermet is formed on the inner wall of the control space 18, and an outer pumping electrode 42 is formed in a portion corresponding to the inner pumping electrode 40 on the upper surface of the first solid electrolyte layer 14a. The inner pumping electrode 40, the outer pumping electrode 42, and the first to third solid electrolyte layers 14a to 14c form an electrochemical pumping cell, i.e. a main pumping cell 44.

In the main pumping cell 44, a desired control voltage (pumping voltage) Vp1 is applied between the inner pumping electrode 40 and the outer pumping electrode 42 by an external first variable power source 46, so that a pumping current Ip0 flows between the inner pumping electrode 40 and the outer pumping electrode 42 in the positive or negative direction. Thus, oxygen in the control space 18 is pumped to the outside, or alternatively external oxygen is pumped into the control space 18, to control the oxygen concentration (partial pressure) in the control space 18.

The buffer space 16, the first partition wall 28, the second partition wall 30, the first slits 34, and the second slits 36 provide the following effect.

In general, oxygen is rapidly introduced from a gas inlet into an internal space of a sensor element due to pulsation of an external exhaust gas. However, in this embodiment, the external oxygen is not introduced directly into the internal space (processing space), and the oxygen is introduced through the first slits 34 into the buffer space 16 and further introduced through the second slits 36 into the control space 18. Therefore, the rapid oxygen concentration change by exhaust gas pulsation can be counteracted by the buffer space 16, the first slits 34, and the second slits 36, whereby the influence of the pulsation on the control space 18 is substantially negligible small. As a result, the correlation is improved between the oxygen pumping amount in the control space 18 of the main pumping cell 44 and the oxygen concentration of the measurement gas, so that the measurement accuracy can be improved, and the control space 18 can be used also as a sensor for detecting air-fuel ratio, etc. To obtain the effect advantageously, each of the first and second slits 34 and 36 formed on the first and second partition walls 28 and 30 preferably has a width of 10 µm or less.

By forming the clogging-preventive space 24 opening outward at the distal end of the sensor element 12, the inlets of the buffer space 16 can be prevented from clogging with particles of soot, oil combustion waste, or the like in the external measurement gas introduced through the gas inlet 26. As a result, a NOx component can be measured with higher accuracy.

The inner pumping electrode 40 and the outer pumping electrode 42 in the main pumping cell 44 generally contain a porous cermet, for example, composed of a metal such as Pt and a ceramic material such as $ZrO_2$. The inner pumping electrode 40 is placed in the control space 18 and brought into contact with the measurement gas, and thereby should be composed of a material that causes no changes of the NOx component in the measurement gas, i.e. a material having a low or no decomposing/reducing ability for the NOx component such as NO or $NO_2$. For example, the inner pumping electrode 40 may contain a perovskite compound ($La_3CuO_4$, etc.), a cermet of a ceramic material and a metal having a low catalytic activity (Au, etc.), or a cermet of a ceramic material, a Pt group metal, and a metal having a low catalytic activity (Au, etc.) In this embodiment, the outer pumping electrode 42 is covered with a porous protecting layer 48 containing alumina, etc., whereby the outer pumping electrode 42 is protected while preventing adhesion of an oil component, etc. contained in the external measurement gas.

An auxiliary pumping electrode 50 containing a porous cermet is formed on the inner wall of the measurement space 20. Thus, the auxiliary pumping electrode 50, an appropriate electrode on the outer surface of the sensor element 12 (the outer pumping electrode 42, etc.), and the first to third solid electrolyte layers 14a to 14c form an auxiliary electrochemical pumping cell, i.e. an auxiliary pumping cell 52, to control the oxygen concentration (partial pressure) in the measurement space 20.

The auxiliary pumping electrode 50 is composed of a material having a low or no decomposing/reducing ability for the NOx component in the measurement gas, like the inner pumping electrode 40 in the main pumping cell 44. For example, the auxiliary pumping electrode 50 may contain a porous cermet composed of Pt (platinum) and $ZrO_2$ with 1% of Au (gold).

In this embodiment, a detecting electrode 54 is formed in the measurement space 20. The detecting electrode 54, the outer pumping electrode 42, the first to third solid electrolyte layers 14a to 14c form an electrochemical pumping cell, i.e. a measuring pumping cell 56, whereby oxygen generated by decomposition of nitrogen oxide (NOx) around the detecting electrode 54 is pumped out and the amount of the oxygen is detected.

As shown in FIG. 2, the detecting electrode 54 is covered with an electrode-protecting layer 58 of a porous ceramic containing alumina in the measurement space 20. Thus, the detecting electrode 54 can be protected while preventing adhesion of an inert component such as a metal, etc. emitted from the auxiliary pumping electrode 50 in the measurement space 20, and the catalytic activity (the NOx-decomposing/reducing ability) of the detecting electrode 54 can be efficiently maintained.

In the sensor element 12, a reference electrode 60, which can be in contact with a reference gas in the reference gas inlet path 22, is formed on the side opposite to the measurement space side on the third solid electrolyte layer 14c.

The reference electrode 60 is formed on a sealing layer of the fourth solid electrolyte layer 14d, and is covered with a porous alumina layer 62 for introducing air. The reference gas in the reference gas inlet path 22 is brought through the porous alumina layer 62 into contact with the reference electrode 60.

By using the reference electrode 60, the oxygen concentration (partial pressure) in the control space 18 or the measurement space 20 can be measured.

Thus, in this embodiment, the inner pumping electrode 40 in the main pumping cell 44, the reference electrode 60, and the first to fourth solid electrolyte layers 14a to 14d form a first oxygen partial pressure-detecting cell 64 for controlling the main pumping cell 44, to detect the oxygen concentration (partial pressure) in the control space 18.

Further, the auxiliary pumping electrode 50 in the auxiliary pumping cell 52, the reference electrode 60, and the first to fourth solid electrolyte layers 14a to 14d form a second oxygen partial pressure-detecting cell 66 for controlling the auxiliary pumping cell 52, to detect the oxygen partial pressure in the measurement space 20. The voltage of a second variable power source 68 is controlled by the second oxygen partial pressure-detecting cell 66. The second variable power source 68 is used for operating the auxiliary pumping cell 52, and its pumping current Ip1 is used for controlling an electromotive force V0 in the first oxygen partial pressure-detecting cell 64.

Further, the detecting electrode 54, the reference electrode 60, and the first to fourth solid electrolyte layers 14a to 14d form a third oxygen partial pressure-detecting cell 70, to detect the oxygen partial pressure around the detecting electrode 54.

A third variable power source 72 is controlled based on an electromotive force V2 detected in the third oxygen partial pressure-detecting cell 70. The third variable power source 72 is used for operating the measuring pumping cell 56, to obtain a pumping current Ip2 corresponding to the nitrogen oxide concentration of the measurement gas.

The outer pumping electrode 42, the reference electrode 60, and the first to fourth solid electrolyte layers 14a to 14d form an electrochemical sensor cell 74. The oxygen partial pressure (concentration) of the external measurement gas can be detected based on an electromotive force Vref obtained by the sensor cell 74.

As shown in FIG. 2, in the sensor element 12, a plurality of ceramic layers, i.e. the fourth to sixth solid electrolyte layers 14d to 14f are stacked and integrated on the side of the third solid electrolyte layer 14c opposite to the side having the internal spaces (16, 18, 20). A heater layer 76, which generates heat under a power from an external source, is vertically interposed between the adjacent fourth and fifth solid electrolyte layers 14d, 14e.

The heater layer 76 is used for heating the first to sixth solid electrolyte layers 14a to 14f in the sensor element 12 at a predetermined temperature to increase the oxygen ion conductivity thereof. A heater element 78 is vertically interposed between electric insulating layers composed of alumina, etc., whereby the heater element 78 is electrically insulated from the fourth and fifth solid electrolyte layers 14d, 14e. A pressure diffusion hole 80 passes through the fourth solid electrolyte layer 14d in the proximal side of the sensor element 12, and the heater layer 76 is communicated by the pressure diffusion hole 80 to the reference gas inlet path 22, to relax an increased inner pressure in the heater layer 76. Further, the heater element 78 in the heater layer 76 is communicated with the surface of the sensor element via an insulated through-hole 82 penetrating through the fifth and sixth solid electrolyte layers 14e, 14f, and electrically connected to one of connector pads 84 insulated from the sixth solid electrolyte layer 14f. The heater element 78 in the heater layer 76 heats at least the first to third solid electrolyte layers 14a to 14c separating the control space 18 and the measurement space 20 at a predetermined temperature.

The nitrogen oxide (NOx) concentration of the measurement gas is detected by the gas sensor 10 of this embodiment as follows. First, the external measurement gas is introduced from the clogging-preventive space 24 at the distal end of the sensor element 12 through the first slits 34 formed on the upper and lower surfaces of the first partition wall 28 into the buffer space 16, and is further introduced through the second slits 36 formed on the upper and lower surfaces of the second partition wall 30 into the control space 18. Then, the voltage of the first variable power source 46 is controlled, whereby the pumping current Ip0 of the main pumping cell 44 is controlled, to stabilize the electromotive force V0 in the first oxygen partial pressure-detecting cell 64. In this process, the oxygen partial pressure in the control space 18 is adjusted at a predetermined value, e.g. about $10^{-7}$ atm.

The measurement gas is introduced from the control space 18 through the third slits 38 formed on the upper and lower surfaces of the third partition wall 32 into the measurement space 20. The voltage of the second variable power source 68 is controlled based on an electromotive force V1 detected by the second oxygen partial pressure-detecting cell 66, and an oxygen pumping operation is carried out by the auxiliary pumping cell 52 under a power from the second variable power source 68, so that the oxygen partial pressure in the measurement space 20 is reduced to the extent that the oxygen has substantially no effect on the NOx measurement. The pumping current Ip1 of the auxiliary pumping cell 52 is input as a control signal into the first oxygen partial pressure-detecting cell 64 to control its electromotive force V0, whereby the gradient of the oxygen partial pressure is stabilized in the measurement space 20 over the third slits 38 and the auxiliary pumping electrode 50.

Further, the gas having the oxygen partial pressure controlled in the measurement space 20 is introduced through the electrode-protecting layer 58 to the detecting electrode 54 under a predetermined diffusion resistance. The NOx in the gas is reduced or decomposed around the detecting electrode 54 to produce oxygen.

Thus produced oxygen is pumped by the measuring pumping cell 56. In this step, the voltage of the third variable power source 72 is controlled to stabilize the electromotive force V2 in the third oxygen partial pressure-detecting cell 70. The amount of the oxygen produced around the detecting electrode 54 is proportional to the NOx concentration of the measurement gas, and thus the NOx concentration can be calculated using the pumping current Ip2 in the measuring pumping cell 56.

Lead wires from the above electrodes and heater are introduced outside, and are electrically connected to corresponding connector pads 84, respectively, as shown in FIG. 3.

The housing 13 shown in FIG. 1 contains three ceramic supporting members (first to third supporting members 86a to 86c) for supporting longitudinal intermediate portions of the sensor element 12, and a connector 88 for supporting the rear end of the sensor element 12 and for electrically connecting the connector pad 84 formed on the solid electrolyte body 11 to the outside. A protective cover 90 is attached to the distal end of the housing 13. An inlet hole 92 for introducing the measurement gas into the housing 13 is formed on the protective cover 90.

A space between the first and second supporting members 86a, 86b is filled with a first talc 94a, a space between the second and third supporting members 86b, 86c is filled with a second talc 94b, a bolting portion 96 for mounting is attached to the distal end of the housing 13, an airtight ring 98 is fit between the bolting portion 96 and the housing 13, and a caulking rubber plug 100 is fixed to the rear end of the housing 13. By using such a structure, the sensor element 12 can be fixed and airtight-packaged in the housing 13. A lead wire 102 is introduced from an external electric circuit through the rubber plug 100 and electrically connected to the connector 88 in the housing 13. The sensor element 12 is fixed by the first and second talcs 94a, 94b by pressing a talc powder using the first to third supporting members 86a to 86c.

As shown in FIG. 3, in the solid electrolyte body 11 of the gas sensor 10, edge portions in a portion to be supported by the first supporting member 86a are beveled to form first chamfered portions 104a, edge portions in a portion to be supported by the second supporting member 86b are beveled to form second chamfered portions 104b, edge portions in a portion to be supported by the third supporting member 86c are beveled to form third chamfered portions 104c, and edge portions in a portion to be supported by the connector 88 are beveled to form fourth chamfered portions 104d. Further, the widths W of the first to fourth chamfered portions 104a to 104d (shown in FIGS. 4A and 4B) are within a range of 30 to 240 μm.

Figure 4A:
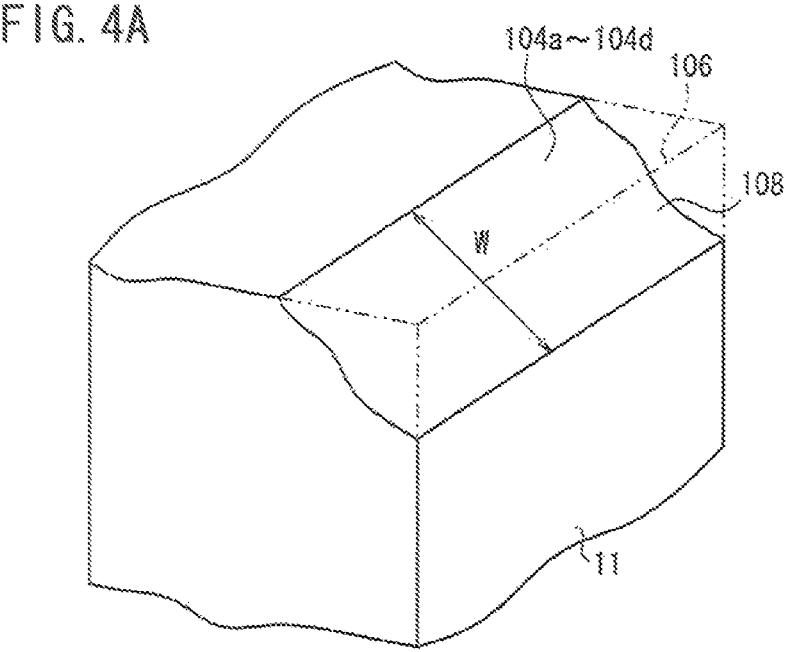
FIGS. 4A and 4B are views for explaining width of chamfered portions.
Figure 4B:
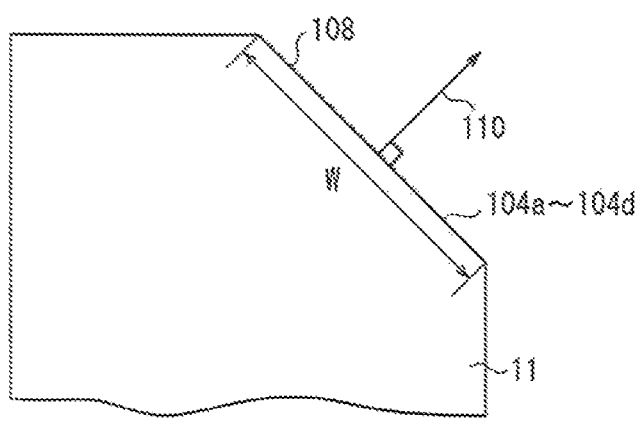

As shown in FIGS. 4A and 4B, the width W of each of the first to fourth chamfered portions 104a to 104d means the length of a C surface (flat surface) 108 in the direction perpendicular to a normal line 110 (see FIG. 4B). The flat surface is formed in the chamfering process by cutting the corner of an edge portion 106 represented by an imaginary line (a two-dot chain line).

Figure 5A:
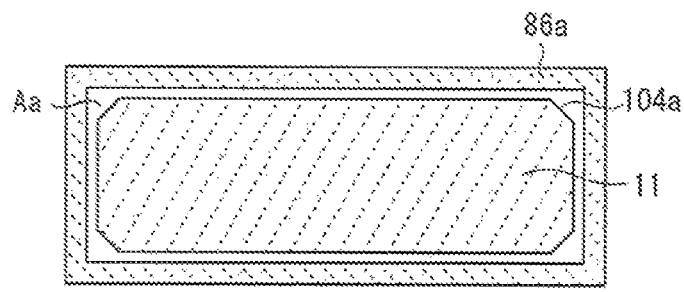
FIG. 5A is a cross-sectional view for explaining a first space area.
Figure 5B:
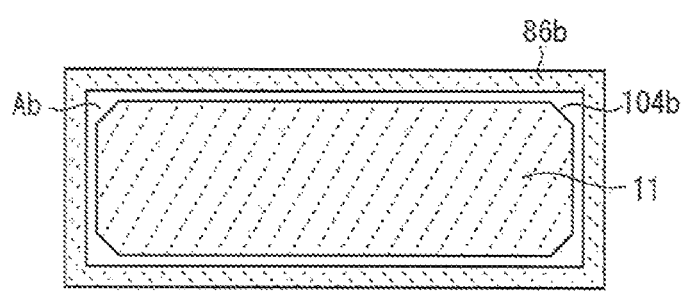
FIG. 5B is a cross-sectional view for explaining a second space area.
Figure 5C:
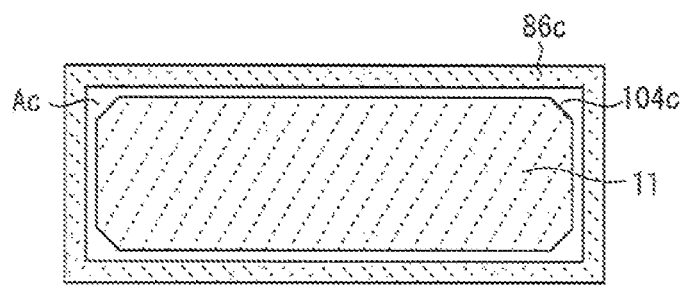
FIG. 5C is a cross-sectional view for explaining a third space area.

In this embodiment, as shown in FIG. 5A, when Aa represents the cross-sectional area of a space formed between the first supporting member 86a and the portion in the solid electrolyte body 11 corresponding to the first supporting member 86a (the first space area), as shown in FIG. 5B, Ab represents the cross-sectional area of a space formed between the second supporting member 86b and the portion in the solid electrolyte body 11 corresponding to the second supporting member 86b (the second space area) and as shown in FIG. 5C, Ac represents the cross-sectional area of a space formed between the third supporting member 86c and the portion in the solid electrolyte body 11 corresponding to the third supporting member 86c (the third space area), the first space area Aa, the second space area Ab, and the third space area Ac are within a range of 1.5 to 3.0 mm$^2$.

Figure 5D:
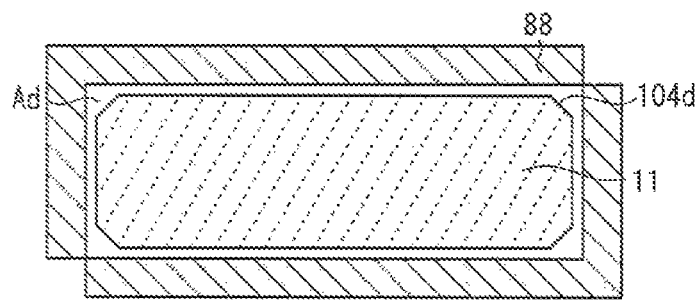
FIG. 5D is a cross-sectional view for explaining a fourth space area.

Further, in this embodiment, as shown in FIG. 5D, when Ad represents the cross-sectional area of a space formed between the connector 88 and the portion in the solid electrolyte body 11 corresponding to the connector 88 (the fourth space area), the fourth space area Ad is within a range of 1.5 to 3.0 mm$^2$.

In the gas sensor 10 of this embodiment, the edge portions 106 corresponding to the first to third supporting members 86a to 86c and the connector 88 are chamfered in this manner in the solid electrolyte body 11 of the sensor element 12. Thus, even when the sensor element 12 is exposed to the measurement gas such as an exhaust gas with a high temperature or when the sensor element 12 is maintained at a high temperature by a heater installed therein, the thermal stress concentration in the solid electrolyte body 11 of the sensor element 12 can be relaxed to improve the thermal shock resistance.

In this embodiment, by controlling the widths of the first to fourth chamfered portions 104a to 104d within the range of 30 to 240 μm in the above chamfering process, the sensor element 12 can be prevented from the breakage by contact with the housing 13 in practical use in an internal combustion engine or the like, to improve the reliability of the gas sensor 10.

Further, by controlling the first to third space areas Aa to Ac within the range of 1.5 to 3.0 mm$^2$, the sensor element 12 can be certainly prevented from being broken by the contact between the solid electrolyte body 11 and the first to third supporting members 86a to 86c.

Furthermore, by controlling the fourth space area Ad within the range of 1.5 to 3.0 mm$^2$, the sensor element 12 can be certainly prevented from being broken by the contact between the solid electrolyte body 11 and the connector 88.

Figure 6:
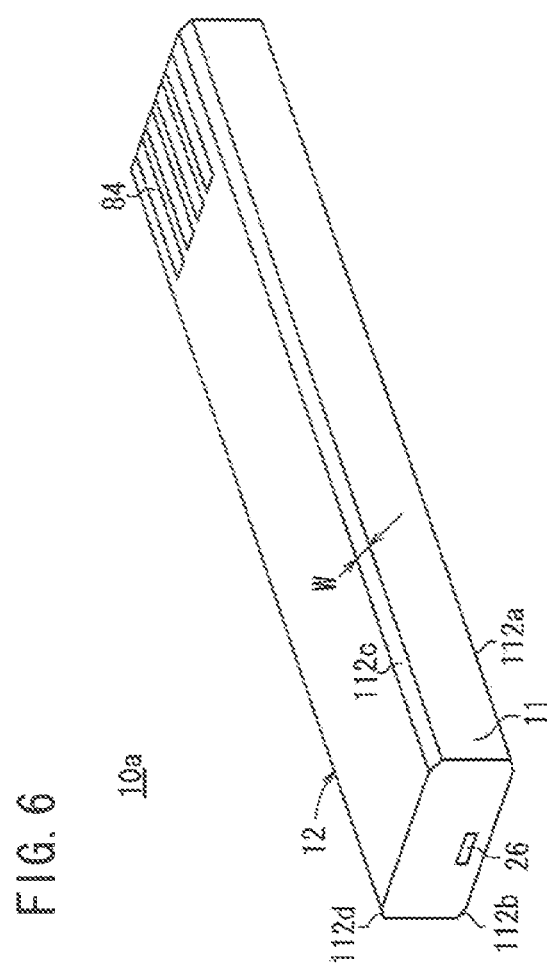
FIG. 6 is a perspective view showing the shape of a solid electrolyte body in a sensor element of a gas sensor according to a modification example.

Though in the above example, edge portions corresponding to the first supporting member 86a are beveled to form the first chamfered portions 104a, the edge portions corresponding to the second supporting member 86b are beveled to form the second chamfered portions 104b, the edge portions corresponding to the third supporting member 86c are beveled to form the third chamfered portions 104c, and the edge portions corresponding to the connector 88 are beveled to form the fourth chamfered portions 104d, four edges of the solid electrolyte body 11 may be chamfered over the entire length of the solid electrolyte body 11 to form a gas sensor 10a according to a modification example as shown in FIG. 6. Thus, eleventh to fourteenth chamfered portions 112a to 112d may be formed on the four edges. In this case, the widths of the eleventh to fourteenth chamfered portions 112a to 112d are preferably within the same range as of the first to fourth chamfered portions 104a to 104d.

In the gas sensor 10a of the modification example, the solid electrolyte body 11 can be easily formed by cutting off the four edges over the entire length, so that the production thereof can be simplified to reduce the production costs.

An experimental example will be described below. In this experimental example, 10 sensor element samples were produced in each of Examples 1 to 3 and Comparative Examples 1 to 3 (total 60 samples), and subjected to a falling test from a height of 2000 mm. The fracture probability of the sensor element 12 was calculated in each Example.

In Example 1, each sample had the structure of the gas sensor 10a according to the modification example (see FIG. 6), and the eleventh to fourteenth chamfered portions 112a to 112d had a width W of 30 μm (the lower limit value). In Example 2, each sample had the structure of the gas sensor 10a, and the eleventh to fourteenth chamfered portions 112a to 112d had a width W of 150 μm (the intermediate value). In Example 3, each sample had the structure of the gas sensor 10a, and the eleventh to fourteenth chamfered portions 112a to 112d had a width W of 240 μm (the upper limit value).

In Comparative Example 1, each sample had the structure of the gas sensor 10a, and the eleventh to fourteenth chamfered portions 112a to 112d had a width W of 0 (not chamfered). In Comparative Example 2, each sample had the structure of the gas sensor 10a, and the eleventh to fourteenth chamfered portions 112a to 112d had a width W smaller than the lower limit value (30 μm). In Comparative Example 3, each sample had the structure of the gas sensor 10a, and the eleventh to fourteenth chamfered portions 112a to 112d had a width W larger than the upper limit value (240 μm).

Figure 7:
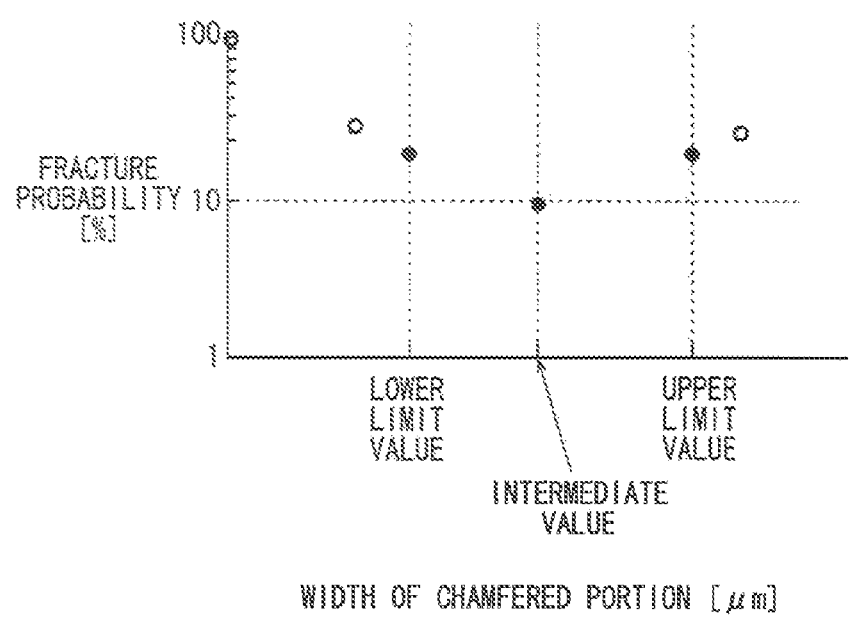
FIG. 7 is a diagram showing plots of measured fracture probabilities versus chamfered portion widths in Examples 1 to 3 and Comparative Examples 1 to 3.

The results of the experimental example are shown in FIG. 7. The results of Comparative Examples 1 to 3 are represented by white circles, and the results of Examples 1 to 3 are represented by black circles. As shown in FIG. 7, the fracture probabilities in Example 1 (approximately 18%) Example 2 (approximately 8%), and Example 3 (approximately 18%) were lower than those in Comparative Example 1 (approximately 100%), Comparative Example 2 (approximately 25%), and Comparative Example 3 (25%), and thus the reliability of the gas sensor was clearly improved in Examples.

It is a matter of course that the gas sensor according to the present invention is not limited to the embodiment described above, which may be embodied in other various forms without deviating from the gist or essential characteristics of the present invention.

What is claimed is:

1. A gas sensor comprising:

a sensor element for detecting a concentration of a specific gas component in a measurement gas; and a housing for supporting said sensor element therein;

wherein said sensor element includes a rectangular solid structure of a ceramic solid electrolyte body, said solid electrolyte body comprising a plurality of dense, airtight, oxygen ion-conductive integrated solid electrolyte layers, a plurality of internal spaces formed between a first, uppermost solid electrolyte layer and a third solid electrolyte layer so that a second solid electrolyte layer defines a spacer between said first and third solid electrolyte layers, said internal spaces being further defined by a plurality of partition walls located between said first and third solid electrolyte layers, wherein upper slits are defined between respective upper ends of said partition walls and said first solid electrolyte layer and lower slits are defined between respective lower ends of said partition walls and said third solid electrolyte layer, wherein said plurality of solid electrolyte layers further comprise fourth to sixth solid electrolyte layers that are stacked and integrated on a side of the third solid electrolyte layer opposing said plurality of internal spaces, and wherein a heater layer is interposed between said fourth and fifth solid electrolyte layers, wherein said sensor element comprises a gas inlet for introducing said measurement gas formed at a distal end of said sensor element between the first and third solid electrolyte layers, an electrode for detecting said gas component located within one of said plurality of internal spaces defining a measurement space, and a lead wire extending rearward from said electrode;

wherein said housing comprises a plurality of supporting members disposed to surround a portion of said sensor element and a connector disposed to surround a rear portion of said sensor element and electrically connected to said lead wire;

wherein a space between said supporting members is filled with talc for fixing said sensor element so that said solid electrolyte body of said sensor element does not contact said supporting members and said connector;

wherein in said solid electrolyte body of said sensor element, at least edge portions corresponding to said supporting members and an edge portion corresponding to said connector are beveled to form chamfered portions having a width of 30 to 240 μm;

wherein a space formed between said supporting members and portions of said solid electrolyte body corresponding to said supporting members has a cross-sectional area of 1.5 to 3.0 mm$^2$;

wherein a space formed between said connector and a portion of said solid electrolyte body corresponding to said connector has a cross-sectional area of 1.5 to 3.0 mm$^2$; and wherein said sensor element does not contact said supporting members and said connector.

2. A gas sensor according to claim 1, wherein four edges of said solid electrolyte body are beveled over an entire length of said solid electrolyte body.

* * * * *